United States Patent [19]

Turner

[11] Patent Number: 4,871,046

[45] Date of Patent: Oct. 3, 1989

[54] DISPOSABLE STETHOSCOPE HEAD SHIELD

[76] Inventor: Kenneth R. Turner, 36 Orchard Rd., Akron, Ohio 44313

[21] Appl. No.: 197,303

[22] Filed: May 23, 1988

[51] Int. Cl.$^4$ ............................................... A61B 7/02
[52] U.S. Cl. ...................................... 181/131; 181/137; 150/154; 206/363; 383/37; 383/66
[58] Field of Search ................ 181/131, 137; 150/154, 150/161, 165; 206/363, 367–369; 383/37, 57, 66

[56] References Cited

U.S. PATENT DOCUMENTS

| | | | |
|---|---|---|---|
| 2,651,380 | 9/1953 | Brandenburg | 181/137 |
| 3,255,841 | 6/1966 | Hasbrouck | 181/126 |
| 3,867,925 | 2/1975 | Ersek | 128/715 |
| 4,344,557 | 8/1982 | Lerner | 383/37 |
| 4,401,125 | 8/1983 | Taylor et al. | 181/131 X |
| 4,461,368 | 7/1984 | Plourde | 181/131 |
| 4,712,684 | 12/1987 | Boeckmann | 383/37 X |

*Primary Examiner*—B. R. Fuller
*Attorney, Agent, or Firm*—Renner, Kenner, Greive, Bobak, Taylor & Weber

[57] ABSTRACT

A disposable shield for stethoscope heads, preventing the transfer of disease or other contaminants by repeated use of the stethoscope. The shield or envelope is formed from a single piece of plastic material in which the sides are folded toward each other, thereby defining two top portions overlying a bottom portion. The edges are sealed as by heat sealing, thereby defining an envelope or shield. In a preferred embodiment, the shields are formed and maintained in a ribbon or array, maintained in the form of a roll within a container or the like. Adjoining shields are interconnected at the heat sealed areas which may be perforated for ease of separation.

14 Claims, 2 Drawing Sheets

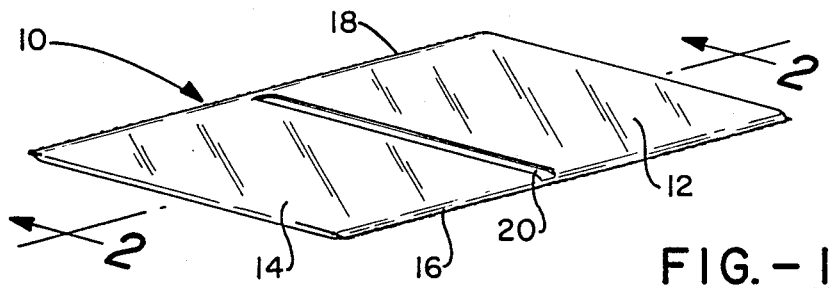
FIG.-1
FIG.-2
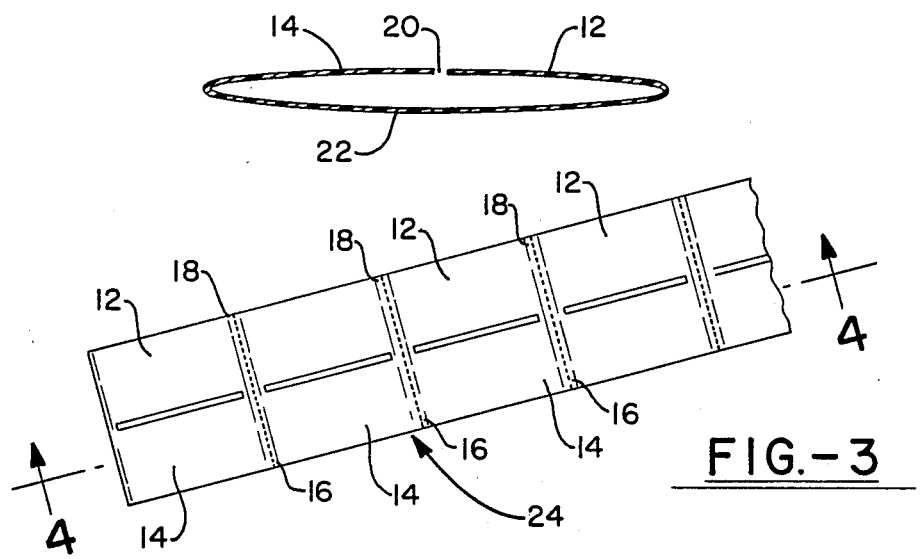
FIG.-3
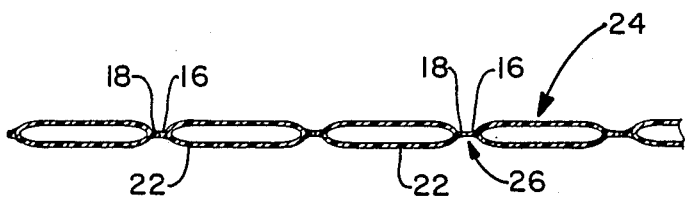
FIG.-4
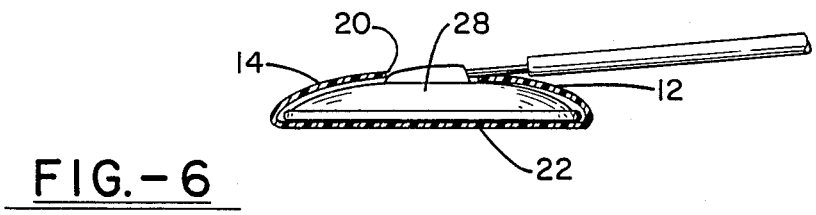
FIG.-6

4,871,046

DISPOSABLE STETHOSCOPE HEAD SHIELD

TECHNICAL FIELD

The invention herein resides in the art of medical equipment and accessories, and more particularly to a shield for the head of a stethoscope which serves to provide a barrier to the passage of body fluids, hair, dirt, skin tissues, and other contaminants from a patient to the stethoscope.

BACKGROUND ART

Heretofore it has been known that stethoscopes are used extensively in medical practice to allow a physician or other care provider to monitor sounds in the respiratory, cardiac, plural, arterial, venus, uterine, fetal, intestinal, and other body systems. The stethoscope is a highly used medical instrument. It is common for physicians or other care providers to constantly have a stethoscope either upon their person or close at hand while in the treating environment. During use, the head of the stethoscope is placed directly on the skin of the patients. Consequently, the entire stethoscope head may become contaminated and be susceptible to passing such contamination to the next patient exposed to the stethoscope head unless the head is sterilized between each use. In practice, physicians and other care providers do not sterilize the stethoscope since such process is extremely time consuming. There is, in fact, no recommended procedure for sterilization of the stethoscope head.

Today, particularly with high incidents of AIDS (Acquired Immune Deficiency Syndrome), it is recommended that the passage of certain body fluids from one individual to another be prohibited. Such fluids include blood, urine, tears, and the like. Since the stethoscope is often placed at points which can transmit such body fluids and contaminants, it is extremely important that the stethoscope head either be sterilized between uses, or be shielded in use such that contaminants will not reach the head itself.

In the prior art, U.S. Pat. No. 4,461,368 teaches a cover for the diaphragm portion of the head of a stethoscope. However, this patent does not provide a barrier along the sides or top portions of the stethoscope head and requires that specific size diaphragm covers be provided and employed. U.S. Pat. No. 3,255,841 teaches a form-fitting rubber or plastic cover with an open portion which, by its very nature, would allow for the type of contamination sought to be prevented by the instant invention. Finally, U. S. Pat. No. 3,867,925 teaches a form of disposable head which must, however, be used in association with an adhesive glue attaching the same to the skin.

DISCLOSURE OF INVENTION

In light of the foregoing, it is the first aspect of the invention to provide a disposable stethoscope head shield which prevents the passage of body fluids and other contaminants from the stethoscope head to the patient and care provider.

Another aspect of the invention is the provision of a disposable stethoscope head shield which is universal in that it can fit any of different styles and shapes of stethoscope heads.

Yet a further aspect of the invention is the provision of a disposable stethoscope head shield colored for ease of location in the care facility.

Still another aspect of the invention is the provision of a disposable stethoscope head shield which requires no adhesives in implementation.

Yet an additional aspect of the invention is the provision of a disposable stethoscope head shield which is easily applied and removed by the care provider.

An additional aspect of the invention is the provision of a disposable stethoscope head shield in which the shield is bidirectional, easily used by both right and left-handed people.

The foregoing and other aspects of the invention which will become apparent as the detailed description proceeds are achieved by a shield for a stethoscope, comprising: a bottom portion; and first and second top portions connected to said bottom portion, said top portions having respective first edges in juxtaposition to each other.

Yet other aspects of the invention which will become apparent are attained by an array of envelopes for receiving the head of a stethoscope, comprising: a sheet of elongate plastic material; side edges of said elongate plastic material folded inwardly toward each other and forming two top portions overlaying a bottom portion, said side edges being in close spaced apart relation to each other; and a plurality of seals in spaced apart relation traversing said sheet and sealing said top portions to said bottom portion.

Yet further aspects of the invention are obtained by an envelope for receiving a stethoscope head, comprising: a sheet of plastic material having sides and ends; said sides of said plastic sheet being folded toward each other, said sides forming top portions overlying a bottom portion; and said ends of said sheet of plastic material being sealed to bond said top portions to said bottom portions.

DESCRIPTION OF DRAWINGS

For a complete understanding of the objects, techniques and structure of the invention, reference should be had to the following detailed description and accompanying drawings wherein:

FIG. 1 is a top perspective view of a stethoscope shield according to the invention;

FIG. 2 is a sectional view of the shield of FIG. 1 taken along the line 2—2;

FIG. 3 is a top perspective view of a web or array of stethoscope shields as shown in FIG. 1;

FIG. 4 is a sectional view of the web or array of FIG. 3 taken along the line 4—4;

FIG. 6 is a sectional view of the stethoscope shield of the invention shown in partial sectional view;

BEST MODE FOR CARRYING OUT THE INVENTION

Figure 5:
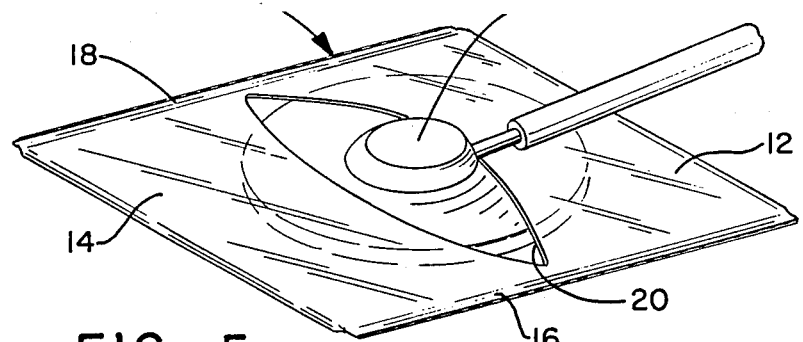
FIG. 5 is a top perspective view of a stethoscope shield according to the invention shown receiving a stethoscope head.

With reference now to the drawings and more particularly FIGS. 1 and 2, it can be seen that a stethoscope shield or sheath made according to the invention is designated generally by the numeral 10. It will be appreciated that the shield 10 is constructed of a unitary piece of plastic film such as polyethylene film. The shield 10 comprises two top portions 12,14, formed by folding side edges of the plastic film toward each other. Appropriate seals 16,18 traverse the sides of the shield 10, sealing the top portions 12,14 to the bottom portion 22. While any of numerous types of seals might be employed, an appropriate heat seal may achieve the desired results, particularly when plastic film constitutes the medium for manufacture of the shield.

It will be noted that the top portions 12,14 are spaced apart from each other a slight amount to define an opening or slit 20 which allows for access to the interior of the shield 10 which is now in the form of an envelope or the like.

As shown in FIGS. 3 and 4, the shields 10 may be presented in the form of a web or ribbon 24. To appreciate how the web 24 is obtained, an understanding of the manufacturing process of the invention should be obtained. In the preferred embodiment, a roll of opaque colored polyethylene film having a thickness of 1-2 mils, and preferably 1.5 mils, is mounted on a feeder roll assembly. In the preferred embodiment, the film has a width of 5-9 inches and, most preferably, 7 inches. The film is drawn over a forming jig which upturns the outer edges simultaneously and folds them inwardly in an axial direction until they are placed in juxtaposition to each other along the center line of the process line or web of film. These edges form the top portions 12,14 of the shield 10. The unfolded portion of the film, upon which the top portions are folded, forms the bottom portion 22 of the shield 10, such being the patient contact portion of the shield. It will, of course, be understood that the total width of the folded film is, in the preferred embodiment, approximately 3.5 inches.

Folded film is next drawn into a heat sealing apparatus, specifically a drum roller with heat sealing elements spaced approximately 2.5 inches on center around the circumference. The range of spacing could be 2-3 inches. A drum of similar diameter applies pressure to the film, forcing it together. Heat is applied, bonding the top and bottom planes of the film together, thus forming the stethoscope shield 10. If bulk packaged items are desired, the temperature of the heating elements is adjusted to seal and melt off the individual shields as they are formed. A vacuum suction device may then transport the shields to a bulk packaging location. If, however, a pocket pack is desired such as will be discussed hereinafter with respect to FIGS. 7 and 8, the formed and sealed ribbon 24 of shields 10 proceeds to a cutting drum where perforations are placed in the center line of each heat sealed bond as by a die cutting operation or the like. The ribbon is then measured and cut to the desired length. The final wind-up device prepares a roll of the ribbon 24 for packaging. Final packaging accordingly consists of a roll of shields sealed in a blister package on a cardboard backing providing an opening through which the shields may be dispensed.

As shown in FIGS. 3 and 4, the ribbon 24 simply comprises a plurality of interconnected shields 20 which may be easily separated as by the perforations 26 introduced thereinto by a die-cutting operation as discussed above.

FIGS. 5 and 6 present the employment of the invention in association with a stethoscope head 28. As shown, the head 28 is inserted through the slit 20 and into the envelope defined by the top portions 12,14 and bottom portion 22, sealed along the lateral edges 16,18. The head 28 substantially fills the envelope from side to side. The seals 16,18 are such as to keep the edges of the top portions 12,14 in close juxtaposition such that, once the head 28 is inserted into the envelope, the slot 20 tightens thereover, substantially enclosing the stethoscope head. In any event the bottom portion of the stethoscope which is placed adjacent the patients body is fully covered by the bottom portion 22.

It will be appreciated that while the stethoscope head shown in FIGS. 5 and 6 is the standard flat type of head, the shields 10 are adapted for use with the bell-shaped stethoscope heads as well.

Figure 7:
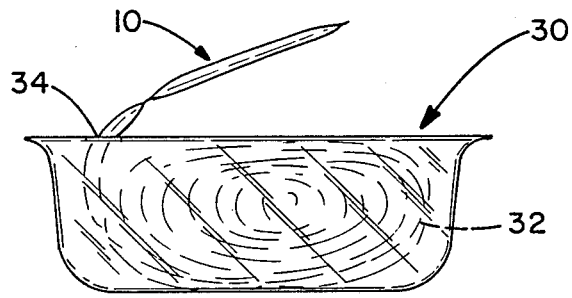
FIG. 7 is an illustrative side sectional view of a container receiving a roll of shields according to the invention and adapted for dispensing the same.
Figure 8:
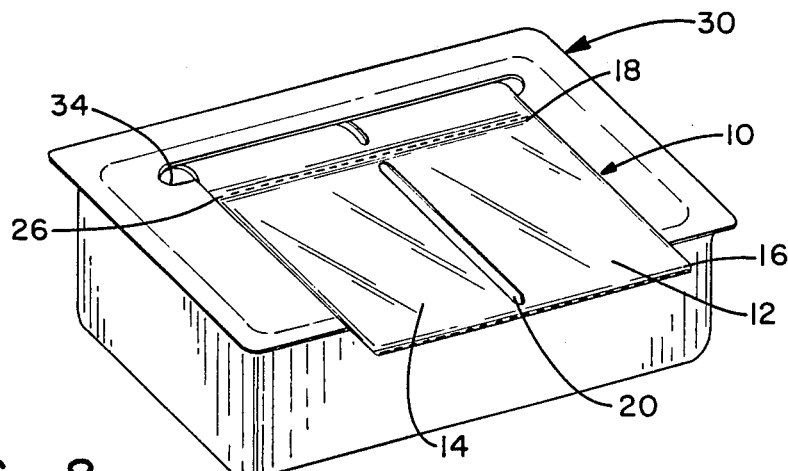
FIG. 8 is a perspective view of the dispensing container of FIG. 7.

As shown in FIGS. 7 and 8, the ribbon 24 of shields 10 may be placed within a container 30 in the form of a roll 32. The shields 10 exit the container 30 through a slot or other appropriate opening 34. The perforations 26 allow for ease of separation of each shield 10 from the adjoining shield. As mentioned above, if the temperature of the sealing mechanism is increased sufficiently, the shields 10 may be separated from each other during the manufacturing process, in which case they may be individually stacked in a bulk container.

It will be appreciated that by making the shields 10 of a colored opaque plastic sheet material, presence of the shield can be most easily detected by the care provider and the patient, giving assurance to both that disease and contaminants are not being transmitted by the stethoscope head. Of course, at the end of each use, the shield 10 is removed and discarded and a new shield put in its place.

In the preferred embodiment of the invention presented above, the shield or envelope 10 is configured as a 3.5×2.5 inch assembly. It will, however, be appreciated that such dimensions may be varied, dependent upon the size of stethoscope head being employed. It will also be appreciated that a shield 10 could, in fact, be made of transparent plastic material if such were desired.

Thus it can be seen that the objects of the invention have been satisfied by the structure presented hereinabove. While in accordance with the patent statutes only the best mode and preferred embodiment of the invention has been presented and described in detail, it will be understood that the invention is not limited thereto or thereby. Accordingly, for an appreciation of the true scope and breadth of the invention, reference should be had to the following claims.

What is claimed is:

1. A shield for a stethoscope, comprising:
   a unitary, continuous, uninterrupted bottom portion; and
   first and second top portions connected to said bottom portion, said top portions having respective first edges in juxtaposition to each other defining an opening therebetween, said top portions being connected to said bottom portion at respective second edges thereof, and said top portions being further connected to said bottom portions at respective third and forth edges thereof, thereby defining an envelope which is sealed except at said opening, said opening being adapted for receiving a head of the stethoscope.

2. The shield according to claim 1 wherein said top and bottom portions comprise a plastic film material.

3. The shield according to claim 2 wherein said third and fourth edges of said portions are heat sealed to said bottom portion.

4. The shield according to claim 3 wherein a plurality of envelopes are provided and said third and fourth edges of said top portions are respectively connected to fourth and third edges of adjacent envelopes, at lines of interconnection.

5. The shield according to claim 4 wherein said lines of interconnection are perforated.

6. The shield according to claim 5 wherein said plastic film is opaque and colored.

7. The shield according to claim 4 wherein said top and bottom portions of said shield and each said adjacent shield are of a continuous sheet of said plastic film material.

8. The shield according to claim 7 wherein said envelope and each said adjacent envelopes are maintained in a roll, said roll received within a dispensing container.

9. The shield according to claim 8 wherein said container has a slot therein from which said envelope and adjacent envelope are dispensed.

10. An array of envelopes for receiving a head of a stethoscope, comprising:
   a sheet of elongate plastic material;
   side edges of said elongate plastic material folded inwardly toward each other and forming two top portions overlaying a bottom portion, said two top portions defining an opening therebetween, said side edges being in close spaced apart relation t other; and
   a plurality of seals in spaced apart relation traversing said sheet and sealing said two top portions to said bottom portion and defining an envelope therebetween, said opening in said envelope between the pairs of seals adapted for receiving the head of the stethoscope.

11. The array of envelopes according to claim 10 wherein said seals include means for separating each envelope from an adjacent envelope.

12. The array of envelopes according to claim 11. wherein said means for separating comprises perforations along said seals.

13. The array of envelopes according to claim 12 which further includes a container receiving each said envelope and adjacent envelope, said container having a slot therein from which said envelopes may be dispensed.

14. An envelope for receiving a stethoscope head, comprising:
   a sheet of plastic material having sides and ends; said sides of said plastic sheet being folded toward each other, said sides forming top portions overlying a bottom portion, said top portions provided with an opening therebetween; and
   said ends of said sheet of plastic material being sealed to bond said top portions to said bottom portions wherein the opening is adapted to receive the stethoscope head.

* * * * *